United States Patent [19]

Felice

[11] 4,397,768
[45] Aug. 9, 1983

[54] SUPPORTED CATALYST FOR THE PREPARATION OF PHTHALIC ANHYDRIDE

[75] Inventor: Klaus M. Felice, Caracas, Venezuela

[73] Assignee: Oxidaciones Organicas, C.A. "OXIDOR", Caracas, Venezuela

[21] Appl. No.: 325,772

[22] Filed: Nov. 30, 1981

Related U.S. Application Data

[63] Continuation-in-part of Ser. No. 211,782, Dec. 1, 1980, abandoned.

[30] Foreign Application Priority Data

Feb. 26, 1981 [DE] Fed. Rep. of Germany ....... 3107320

[51] Int. Cl.$^3$ .................... B01J 21/02; B01J 31/02; B01J 27/14; B01J 35/00
[52] U.S. Cl. .................... 252/432; 252/430; 252/435; 252/477 R
[58] Field of Search .................... 252/430, 432

[56] References Cited

U.S. PATENT DOCUMENTS

| | | | |
|---|---|---|---|
| 2,035,606 | 3/1936 | Jaeger | 23/233 |
| 2,510,803 | 6/1950 | Cooper | 252/464 |
| 2,625,554 | 1/1953 | Darby | 260/342 |
| 2,698,306 | 12/1954 | Matejczyk | 252/464 |
| 2,773,838 | 12/1956 | Reid et al. | 252/437 |
| 2,809,939 | 10/1957 | Dixon et al. | 252/456 |
| 3,055,842 | 9/1962 | Robinson | 252/461 |
| 3,086,026 | 4/1963 | Wiebusch | 260/346.8 |
| 3,156,705 | 11/1964 | Kerr | 260/346.8 |
| 3,156,706 | 11/1964 | Kerr | 260/346.8 |
| 3,215,644 | 11/1965 | Kakinoki et al. | 252/440 |
| 3,288,721 | 11/1966 | Kerr | 252/435 |
| 3,420,750 | 1/1969 | Schaefer et al. | 203/72 |
| 3,464,930 | 9/1969 | Friedrichsen et al. | 252/469 |
| 3,507,813 | 4/1970 | Vrbaski | 252/464 |
| 3,507,886 | 4/1970 | Suter et al. | 260/346.7 |
| 3,509,179 | 4/1970 | Friedrichsen et al. | 260/346.4 |
| 3,559,723 | 2/1971 | Wagner et al. | 165/2 |
| 3,562,185 | 2/1971 | Friedrichsen et al. | 252/456 |
| 3,565,829 | 2/1971 | Friedrichsen et al. | 252/464 |
| 3,566,961 | 3/1971 | Lorenz et al. | 165/159 |
| 3,684,741 | 8/1972 | Friedrichsen et al. | 252/435 |
| 3,686,229 | 8/1972 | Poehler et al. | 260/346.4 |
| 3,692,699 | 9/1972 | Hojo et al. | 252/440 |
| 3,780,011 | 12/1973 | Pullukat et al. | 260/94.9 D |
| 3,799,886 | 3/1974 | Felice et al. | 252/461 |
| 3,830,755 | 8/1974 | Reuter et al. | 252/456 |
| 3,840,563 | 10/1974 | Goehre et al. | 260/346.4 |
| 3,892,781 | 7/1975 | Montgomery et al. | 260/346.4 |
| 3,894,971 | 7/1975 | Reuter et al. | 252/437 |
| 3,898,249 | 8/1975 | Felice et al. | 260/346.4 |
| 3,905,420 | 9/1975 | Wirth et al. | 165/82 |
| 3,909,457 | 9/1975 | Friedrichsen et al. | 252/476 |
| 3,926,846 | 12/1975 | Ono et al. | 252/435 |
| 3,948,807 | 4/1976 | Fuchigami et al. | 252/456 |
| 4,002,198 | 1/1977 | Wagner et al. | 165/61 |
| 4,007,136 | 2/1977 | Blechschmitt et al. | 252/461 |
| 4,036,783 | 7/1977 | Blechschmitt et al. | 252/461 |
| 4,046,780 | 9/1977 | Nakanishi et al. | 260/346.4 |
| 4,052,418 | 10/1977 | Suresh et al. | 549/258 |
| 4,075,231 | 2/1978 | Dolhyj et al. | 260/346.4 |
| 4,076,731 | 2/1978 | Dolhyj et al. | 252/248 |
| 4,077,912 | 3/1978 | Dolhyj et al. | 252/461 |
| 4,077,984 | 3/1978 | Blechschmitt et al. | 260/346.4 |
| 4,096,094 | 6/1978 | Blechschmitt et al. | 252/440 |
| 4,119,645 | 10/1978 | Auroy et al. | 260/346.4 |
| 4,282,116 | 8/1981 | Reuter et al. | 252/461 |
| 4,305,843 | 12/1981 | Krefetz et al. | 252/432 |

FOREIGN PATENT DOCUMENTS

| | | |
|---|---|---|
| 1945727 | 9/1969 Fed. Rep. of Germany | 252/440 |
| 2142838 | 8/1970 Fed. Rep. of Germany | 252/435 |
| 2129790 | 6/1971 Fed. Rep. of Germany | 252/439 |
| 2106796 | 8/1972 Fed. Rep. of Germany | . |
| 2321799 | 4/1973 Fed. Rep. of Germany | 252/440 |
| 2446639 | 9/1974 Fed. Rep. of Germany | 252/435 |
| 2510994 | 9/1976 Fed. Rep. of Germany | . |
| 2547624 | 4/1977 Fed. Rep. of Germany | . |
| 2925682 | 6/1979 Fed. Rep. of Germany | 252/435 |
| 596881 | 10/1977 Switzerland | 252/461 |

*Primary Examiner*—Delbert E. Gantz
*Assistant Examiner*—William G. Wright
*Attorney, Agent, or Firm*—Morgan, Finnegan, Pine, Foley & Lee

[57] ABSTRACT

A catalyst is disclosed comprising an inert carrier supporting a catalytically active mass of vanadium pentoxide, titanium dioxide, promoters and inhibitors for use in the gas phase reaction of ortho-xylene with air to produce phthalic anhydride without addition of sulfur or sulfur dioxide to the ortho-xylene-air mixture.

18 Claims, No Drawings

SUPPORTED CATALYST FOR THE PREPARATION OF PHTHALIC ANHYDRIDE

CROSS-REFERENCE TO RELATED APPLICATIONS

This application is a continuation-in-part of application Ser. No. 211,782, filed Dec. 1, 1980, now abandoned.

BACKGROUND OF THE INVENTION

This invention relates generally to a catalyst for the production of phthalic anhydride from the oxidative treatment of o-xylene with air. More specifically, the catalyst comprises a poreless, mechanically-stable, temperature-resistant, inert carrier to which there is adhered a catalytically active surface coating.

Supported catalysts containing vanadium pentoxide and titanium dioxide in the catalytically active mass have been known for a long time and are used in technical processes for the production of phthalic anhydride. As promoters or inhibitors to this vanadium pentoxide-titanium dioxide mass, nearly all of the oxide forming elements alone, or in different combinations and varying mixing rates, have been described. See for example DOS Nos. 2547624, 2510994 and 2106796.

One disadvantage of existing industrial catalysts is, that to obtain a high yield and a satisfactory quality of phthalic anhydride under commercial operating conditions, the presence of sulfur or sulfur dioxide is required in the feedstock. If not otherwise present, it has to be added to the ortho-xylene air mixture prior to reaction. Most commercial prior art operations require on the order of 0.1 to 0.3% S or 0.2 to 0.6% $SO_2$, by weight, based upon the ortho-xylene used. But the presence of the sulfur compounds gives rise to environmental pollution problems, requiring extra steps to de-sulfurize one or more effluent streams, before release. The alternative, of course, is to pollute the environment, either air or water, with malodorous sulfur compounds. It is, of course, very well known that even trace amounts of sulfur compounds are easily detectable by the senses and are harmful. Hence, prior art systems that require addition of sulfur compounds are inherently undesirable.

It is commonly known that the activity and selectivity of a catalyst is closely related, but to date not predictable from its composition, structure, and method of preparation.

SUMMARY OF THE INVENTION

This invention permits the catalytic preparation of phthalic anhydride by a process that does not require the addition of sulfur compounds. Indeed, when using the catalyst systems of this invention, no advantage or benefit is achieved by the presence or addition of sulfur in the feedstock. The catalyst system of this invention requires, in certain ratios, vanadium pentoxide, titanium dioxide, and the oxides of boron, of antimony and of potassium. By means of the sulfur-free systems of this invention, ortho-xylene can be converted, in high yields to phthalic anhydride, of good product quality, and at high ortho-xylene loads of between 130 grams and 290 grams per reaction tube per hour, or more.

DETAILED DESCRIPTION OF THE INVENTION

The catalysts of this invention comprise substantially poreless, mechanically-stable, temperature-resistant, inert carrier particles on which a catalytically active surface coating firmly adheres, the coating containing inorganic materials in the following molar relationship:

Vanadium pentoxide, 1 mole
Potassium oxide, from 0.02 to 0.05 mole
Boron trioxide, from 0.002 to 0.005 mole
Antimony trioxide, from 0.008 to 0.015 mole
Titanium dioxide, from 10 to 15 moles The catalyst coating may, optionally, also contain up to 0.01 mole of phosphorus pentoxide, although, unlike certain prior art compositions, the presence of phosphorus is not required.

While the proportions of the elements in the catalysts are described and calculated as the specific, listed oxides, it is to be understood that in actual use, in the catalyst, the listed metallic element may exist in different forms or combinations or valences.

The substantially poreless, mechanically-stable, temperature-resistant, inert carrier particles used in the catalysts of the invention may comprise such materials as porcelain, steatite, silicon carbide, silicon dioxide, aluminum, aluminum oxide, silicates, aluminates or mixtures thereof. The size and diameter of the particles may vary. There may be used regularly or irregularly formed particles.

The carrier particles preferably used are in ring form having the following dimensions:

| | |
|---|---|
| Length | 7.6 to 8.0 mm |
| Outer diameter | 8.6 to 9.0 mm |
| Wall | 1.2 to 2.3 mm |

The surface coating, which firmly adheres to the carrier particles, has a thickness of about 0.05 to 0.15 mm. The amount of inorganic oxides in the surface coating lies between 4.0 and 6.0 weight percent in relation to the catalyst.

Any common apparatus may be used for the coating of the active mass onto the carrier particles. For instance, an aqueous suspension of the catalytically active components and an organic binder may be sprayed onto the rolling carrier particles in a "drage drum" (drum used for coating). The film coating may very easily be performed in a special film coating apparatus as described in DPS 1280756. The aqueous suspension of the catalytically active components and an organic binder are sprayed through nozzles onto the carrier particles which are held in rolling movement in a preheated air stream of 80° C. to 120° C. The water evaporates in the hot air stream and forms a very uniform and firmly adhering film on the carrier particles.

For the preparation of the aqueous suspension, the oxides of titanium, vanadium and antimony, together with aqueous solutions of boric acid, potassium hydroxide, an organic binder and water, are filled into a ball mill and ground for several hours. Optionally, phosphoric acid may also be included.

Titanium dioxide is used as anatase with a BET surface area of 12 to 16 $m^2/g$. It may be obtained by precipitating voluminous titanium oxide compounds from titanyl sulfate or titanium tetrachloride with water. The precipitate is separated, dried and calcined between 600° and 800° C. The higher the temperature and the longer the calcination time, the lower will be the BET surface area of the anatase. Accordingly, one can easily obtain an anatase of the desired BET surface area by adjusting calcination temperature and time.

A mixture of two anatase types of different BET surface areas may also be used. To obtain an average BET surface area of 12 to 16 m$^2$/g, a commercially available anatase of a surface area between 8 and 10 m$^2$/g is blended with an anatase of a surface area between 15 and 40 m$^2$/g produced in the above-described manner.

For the preparation of the aforedescribed suspension, instead of the oxides, acids or hydroxides, other compounds of said elements may be used, such as oxalates, carbonates, acetates or ammonium salts.

Suitable organic binders for purposes of this invention are highly fillable copolymer dispersions of the type vinylacetate-vinyllaurate, vinylacetate-acrylate, styrene-acrylate, vinylacetate-maleate or vinylacetate-ethylene. An addition of 15% to 25% of organic matter in relation to the inorganic components is generally sufficient.

The catalyst produced in a film coating apparatus is very resistant to abrasion; this is a very positive feature for the transport and filling of the catalyst into the reaction tubes.

The BET surface area of the active mass of a freshly prepared catalyst according to this invention is practically zero (non-measurable). After heating the catalyst for several hours in an air stream of 400° C., whereby the organic substances burn off, the catalytically active surface coating shows a BET surface area of approximately 12 to 14 m$^2$/g.

The gas phase reaction of ortho-xylene with air using the catalyst of the invention is usually performed in known reactors of approximately 3 m reaction tube length and 25 mm inner reaction tube diameter, the resulting heat being led off by a salt melt.

The preferred amount of air per tube per hour is from 3 to 4.5 Nm$^3$. An air flow of 4 Nm$^3$ creates a pressure drop across the reactor of only approximately 2 m water gauge when using rings of above-given dimensions and a filling height of 2.8 m in the reactor. At optimal salt bath temperature, being usually between 375° C. and 385° C., the catalysts give extraordinarily good yields of phthalic anhydride working with an ortho-xylene load of between 130 g and 290 g per tube per hour. The quality of the crude phthalic anhydride, despite no addition of sulfur or sulfur dioxide to the ortho-xylene/air mixture, is excellent. The phthalide content in crude phthalic anhydride, crystallized at 60° C. in a finned tube switch condenser and afterwards melted, is below 0.1%.

EXAMPLE

Preparation of Catalysts

The surface coating of all catalysts was performed in a film coating apparatus at an air stream temperature between 80° C. and 120° C. For the preparation of the suspension, which was sprayed onto the carrier particles, the oxides of titanium, vanadium and antimony together with a 5% aqueous solution of boric acid, a 10% aqueous solution of potassium hydroxide, a vinylacetate-acrylate copolymer dispersion and water, were filled into a ball mill and ground overnight (15 to 20 hours).

The titanium dioxide used in Example 1 of Table I and Example 10 of Table II was an anatase of a BET surface area of 15 m$^2$/g obtained from the precipitation of titanyl-sulfate after drying and calcination. In all other examples the titanium dioxide was always a blend of three parts of commercially available anatase with a surface area of approximately 9 m$^2$/g, and one part of an anatase obtained from the precipitation of titanyl-sulfate. After drying and calcination, this anatase showed a BET surface area of approximately 25 m$^2$/g.

In the preparation of the examples in Table II with the exception of Example 13, phosphoric acid was employed as a reactant.

The weight ratio of inorganic compounds, expressed as oxides, to the organic binder was kept 4 to 1.

The amount of water was chosen so that the viscosity of the suspension, measured at 20° with a viscosity beaker, gave figures between 12 and 15 DIN/sec.

The molar composition of the inorganic oxides in the catalytically active surface coating related to vanadium pentoxide equalling one mole, as well as the weight percentages of vanadium pentoxide in the finished catalyst, is given in Tables I and II.

As carrier, steatite rings of the following dimensions were used in all cases:

| | |
|---|---|
| Length | 7.8 mm |
| Outer diameter | 8.8 mm |
| Wall | 2.0 mm |

The spraying process in the film coating apparatus may be interrupted several times for weight control. The film contains, besides the catalytically active components, organic matter which can easily be detected and calculated by the loss of weight during heating of a sample of the catalyst in an air stream of 400° C. The amount of inorganic oxides can then be easily calculated.

Oxidation Process

All tests were performed in single tube reactors 3.3 m in length and 25 mm inner reaction tube diameter. The filling height of the catalyst in each case was 2.8 m. In order to burn out the organic matter, all catalysts were heated to 380° C. in an air stream of 1 Nm$^3$ per tube per hour. When the salt bath temperature of 380° C. was reached, the amount of air was increased to 4 Nm$^3$ per tube per hour before feeding orthoxylene to the reactor. During the first two weeks of each trial, the ortho-xylene load was increased stepwise from initially 180 g per tube per hour to 250 g per tube per hour, and then maintained constant for at least two more weeks.

For comparison, all catalysts were tested at a constant salt bath temperature of 380° C., on one occasion without addition of sulfur to the ortho-xylene, and on another with addition of 0.1 weight percent sulfur related to the ortho-xylene. The yield figures in Tables I and II signify kilograms of crude phthalic anhydride, precipitated in switch condensers at approximately 60° C. and afterwards fused out, related to kilograms of pure ortho-xylene consumed during the same period of time. These figures are averaged figures over two weeks, not including the start-up period of two weeks.

The phthalide figures in Tables I and II were determined gas chromatographically in the crude phthalic anhydride.

TABLE I

| | Data of Catalyst | | | | | | Test Data | | |
|---|---|---|---|---|---|---|---|---|---|
| | $V_2O_5$ in Catalyst | Molar composition of Inorganic Oxides in surface layer (related to $V_2O_5$ equalling one mole) | | | | | Sulfur in ortho-xylene | Crude P.A. Yield | Phthalide in Crude P.A. |
| | Weight % | $K_2O$ | $B_2O_3$ | $Sb_2O_3$ | $TiO_2$ | $V_2O_5$ | Weight % | Weight % | Weight % |
| Number of catalyst or Example | | | | | | | | | |
| 1 | 0.9 | 0.035 | 0.0035 | 0.012 | 12.5 | 1 | 0.0 | 111.6 | 0.05 |
| | | | | | | | 0.1 | 111.4 | 0.05 |
| 2 | 0.9 | 0.035 | 0.0035 | 0.012 | 12.5 | 1 | 0.0 | 111.8 | 0.04 |
| | | | | | | | 0.1 | 111.5 | 0.05 |
| 3 | 0.8 | 0.05 | 0.005 | 0.015 | 15 | 1 | 0.0 | 110.8 | 0.08 |
| | | | | | | | 0.1 | 110.7 | 0.07 |
| 4 | 1.0 | 0.02 | 0.002 | 0.010 | 10 | 1 | 0.0 | 110.9 | 0.08 |
| | | | | | | | 0.1 | 110.8 | 0.09 |
| COMPARISON EXAMPLES | | | | | | | | | |
| 5 | 0.9 | 0.035 | — | 0.012 | 12.5 | 1 | 0.0 | 108.7 | 0.24 |
| | | | | | | | 0.1 | 109.2 | 0.18 |
| 6 | 0.9 | 0.035 | 0.0035 | — | 12.5 | 1 | 0.0 | 107.9 | 0.25 |
| | | | | | | | 0.1 | 108.2 | 0.20 |
| 7 | 0.9 | — | 0.0035 | 0.012 | 12.5 | 1 | 0.0 | 109.8 | 0.02 |
| | | | | | | | 0.1 | 109.9 | 0.03 |

TABLE II

| | Data of Catalyst | | | | | | | Test Data | | |
|---|---|---|---|---|---|---|---|---|---|---|
| | $V_2O_5$ in Catalyst | Molar composition of Inorganic Oxides in surface layer (related to $V_2O_5$ equalling one mole) | | | | | | Sulfur in ortho-xylene | Crude P.A. Yield | Phthalide in Crude P.A. |
| | (Weight %) | $K_2O$ | $B_2O_3$ | $P_2O_5$ | $Sb_2O_3$ | $TiO_2$ | $V_2O_5$ | (Weight %) | (Weight %) | (Weight %) |
| Number of Catalyst | | | | | | | | | | |
| 8 | 0.8 | 0.05 | 0.005 | 0.01 | 0.015 | 15 | 1 | 0.0 | 110.7 | 0.09 |
| | | | | | | | | 0.1 | 110.6 | 0.08 |
| 9 | 1 | 0.02 | 0.002 | 0.002 | 0.008 | 10 | 1 | 0.0 | 110.8 | 0.07 |
| | | | | | | | | 0.1 | 110.6 | 0.06 |
| 10 | 0.9 | 0.04 | 0.003 | 0.006 | 0.011 | 12.5 | 1 | 0.0 | 111.2 | 0.05 |
| | | | | | | | | 0.1 | 111.0 | 0.06 |
| 11 | 0.9 | 0.04 | 0.003 | 0.006 | 0.011 | 12.5 | 1 | 0.0 | 111.4 | 0.04 |
| | | | | | | | | 0.1 | 111.2 | 0.05 |
| COMPARISON EXAMPLES | | | | | | | | | | |
| 12 | 0.9 | 0.04 | — | 0.006 | 0.11 | 12.5 | 1 | 0.0 | 108.8 | 0.12 |
| | | | | | | | | 0.1 | 109.5 | 0.09 |
| 13 | 0.9 | 0.04 | — | — | 0.11 | 12.5 | 1 | 0.0 | 108.0 | 0.18 |
| | | | | | | | | 0.1 | 109.1 | 0.11 |
| 14 | 0.9 | 0.04 | 0.003 | 0.006 | — | 12.5 | 1 | 0.0 | 107.8 | 0.25 |
| | | | | | | | | 0.1 | 108.4 | 0.16 |

It should be understood by those skilled in the art that various modifications may be made in the present invention without departing from the spirit and scope thereof as described in the specification and defined in the appended claims.

What is claimed is:

1. A catalyst capable of producing phthalic anhydride from o-xylene in the substantial absence of sulfur compounds, consisting essentially of a substantially poreless, mechanically-stable, temperature-resistant, inert carrier to which there is adhered a catalytically active surface coating containing the following components in the following proportions, calculated as the oxides, in relation to one mole of vanadium pentoxide; potassium oxide, from about 0.02 to 0.05 mole; boron trioxide, from about 0.002 to 0.005 mole; antimony trioxide, from about 0.008 to 0.015 mole; and titanium dioxide, from about 10 to 15 moles.

2. A catalyst as claimed in claim 1 wherein the vanadium content calculated as vanadium pentoxide, in the finished catalyst, is from about 0.6 to 1.2 weight percent.

3. A catalyst as in claim 2, where the said surface coating contains up to about 0.01 mole of phosphorus, calculated as $P_2O_5$.

4. A catalyst as claimed in claim 2 wherein said inert carrier is selected from among porcelain, steatite, silicon carbide, aluminum, a silicate, an aluminate, and mixtures thereof.

5. A catalyst as claimed in claim 4, in the form of rings, having the dimensions: length from 7.6 mm to 8.0 mm; outer diameter from 8.6 mm to 9.0 mm; and wall thickness from 1.2 mm to 2.3 mm.

6. A catalyst as claimed in claim 1 wherein the catalytically active surface coating, after a five hour heat treatment at 400° C. in an air stream, has a BET surface area of between about 11 and 15 m²/g.

7. A process for preparing a catalyst as claimed in claim 1 which comprises air-spraying on to an inert carrier an aqueous suspension consisting essentially of titanium dioxide, vanadium pentoxide, antimony trioxide, boric acid, potassium hydroxide and an organic binder, said suspension having a viscosity of from about 12 to 15 DIN/sec. when measured at 20° C.

8. A process as claimed in claim 7 wherein said air spraying is carried out at an air-stream temperature of from 80° C. to 120° C.

9. A process as claimed in claim 7 wherein the weight ratio of inorganic compounds, expressed as oxides, to said organic binder is from about 3:1 to about 5:1.

10. A process as claimed in claim 9 wherein said organic binder is a copolymer selected from vinylacetate-vinyllaurate, vinylacetate-acrylate, styrene-acrylate, vinylacetate-maleate, or vinylacetate-ethylene.

11. A process as claimed in claim 7 wherein said air-sprayed aqueous suspension is obtained by combining titanium dioxide (anatase) having a BET surface area of between about 12 and 16 $m^2/g$, vanadium pentoxide, antimony pentoxide, boric acid, potassium hydroxide, an organic binder and water.

12. A process as claimed in claim 7 wherein said air-sprayed aqueous suspension is obtained by combining titanium dioxide (anatase) as a blend of a titanium dioxide having a BET surface area between about 8 and 10 $m^2/g$ and a titanium dioxide having a BET surface area between about 15 and 40 $m^2/g$, said blend having an average surface area between about 12 and 16 $m^2/g$, vanadium pentoxide, antimony pentoxide, boric acid, potassium hydroxide, an organic binder and water.

13. A process for preparing a catalyst as claimed in claim 3 which comprises air-spraying onto an inert carrier an aqueous suspension consisting essentially of titanium dioxide, vanadium pentoxide, antimony trioxide, boric acid, phosphoric acid, potassium hydroxide and an organic binder, said suspension having a viscosity of from about 12 to 15 DIN/sec. when measured at 20° C.

14. A process as claimed in claim 13 wherein said air spraying is carried out at an air-stream temperature of from 80° C. to 120° C.

15. A process as claimed in claim 13 wherein the weight ratio of inorganic compounds, expressed as oxides, to said organic binder is from about 3:1 to about 5:1.

16. A process as claimed in claim 15 wherein said organic binder is a copolymer selected from vinylacetate-vinyllaurate, vinylacetate-acrylate, styrene-acrylate, vinylacetate-maleate or vinylacetate-ethylene.

17. A process as claimed in claim 13 wherein said air-sprayed aqueous suspension is obtained by combining titanium dioxide (anatase) having a BET surface area of between about 12 and 16 $m^2/g$, vanadium pentoxide, antimony trioxide, boric acid, phosphoric acid, potassium hydroxide and an organic binder.

18. A process as claimed in claim 13 wherein said air-sprayed aqueous suspension is obtained by combining titanium dioxide (anatase) as a blend of a titanium dioxide having a BET surface area between about 8 and 10 $m^2/g$ and a titanium dioxide having a BET surface area between about 15 and 40 $m^2/g$, said blend having an average surface area between about 12 and 16 $m^2/g$, vanadium pentoxide, antimony trioxide, boric acid, phosphoric acid, potassium hydroxide and an organic binder.

* * * * *